United States Patent [19]

Van Leeuwen et al.

[11] Patent Number: 5,454,825
[45] Date of Patent: Oct. 3, 1995

[54] CIRCULAR ANASTOMOSIS DEVICE WITH SEAL

[75] Inventors: Timothy O. Van Leeuwen, Brookfield; Philip D. Calabrese, Danbury; Frank J. Viola, Sandy Hook, all of Conn.

[73] Assignee: United States Surgical Corporation, Norwalk, Conn.

[21] Appl. No.: 130,607

[22] Filed: Oct. 1, 1993

[51] Int. Cl.⁶ .................................................. A61B 17/00
[52] U.S. Cl. ......................... 606/151; 227/175; 227/179
[58] Field of Search .................................. 606/142, 143, 606/151, 153, 213, 215; 227/175–181, 19, 901

[56] References Cited

U.S. PATENT DOCUMENTS

| | | | |
|---|---|---|---|
| 4,027,510 | 6/1977 | Hiltebrandt . | |
| 4,104,905 | 8/1978 | Zachary | 73/40 |
| 4,316,624 | 2/1982 | Daulin | 285/158 |
| 4,485,817 | 12/1984 | Swiggett | 227/180 |
| 4,488,523 | 12/1984 | Shichman | 227/179 |
| 4,576,167 | 3/1986 | Noiles . | |
| 4,796,899 | 1/1989 | Herrick et al. | 227/228 |
| 4,843,835 | 7/1989 | Goetz et al. | 62/285 |
| 5,005,749 | 4/1991 | Aranyi . | |
| 5,040,715 | 8/1991 | Green et al. . | |
| 5,076,188 | 12/1991 | Burroughs | 114/201 |
| 5,084,057 | 1/1992 | Green et al. . | |
| 5,100,420 | 3/1992 | Green et al. . | |
| 5,119,983 | 6/1992 | Green et al. . | |
| 5,122,276 | 6/1992 | Loikits | 210/663 |
| 5,125,553 | 6/1992 | Oddsen et al. . | |
| 5,158,222 | 10/1992 | Green et al. . | |
| 5,171,249 | 12/1992 | Stefanchik et al. . | |
| 5,197,649 | 3/1993 | Bessler et al. | 227/179 |
| 5,201,339 | 4/1993 | Buchan et al. | 137/268 |
| 5,333,773 | 8/1994 | Main et al. . | |
| 5,364,001 | 11/1994 | Bryan . | |
| 5,364,002 | 11/1994 | Green et al. . | |

*Primary Examiner*—Stephen C. Pellegrino
*Assistant Examiner*—Jeffrey A. Schmidt

[57] ABSTRACT

A surgical instrument for performing a circular anastomosis is disclosed. The instrument is provided with sealing means to permit use during endoscopic procedures. The first seal is fabricated from polyethylene foam, is disposed about an elongate member and is in at least partial contact with an inner surface of a compression member. The second seal is an O-ring seal configured and dimensioned to at least partially contact an outer portion of the compression member and an inner portion of an outer tube. The second seal is disposed intermediate of the compression member.

5 Claims, 2 Drawing Sheets

CIRCULAR ANASTOMOSIS DEVICE WITH SEAL

BACKGROUND OF THE INVENTION

1. Field of the Invention

The present invention relates to surgical instruments for applying surgical staples to body tissue, and more particularly to a sealed apparatus for applying an annular array of surgical staples.

2. Discussion of the Related Art

Surgical stapling devices for applying an annular array of staples to tissue are well known in the art. These devices typically include a stapling assembly and an anvil member at the distal end of the apparatus. The stapling assembly generally includes a circular array of staples and means for expelling the staples against the anvil member. The anvil member typically includes means for completing the circular anastomosis, i.e. an array of bucket-shaped members against which the staples are formed after being expelled from the stapling assembly.

Surgical stapling devices for applying an annular array of staples are well known in gastric and esophageal surgery, for example, in classic or modified gastric reconstruction typically formed in an end-to-end, end-to-side or side-to-side manner. One such instrument is the Premium CEEA® surgical stapler, manufactured and sold by United States Surgical Corporation. In use, the instrument typically is positioned within the lumen of an organ such as the stomach, esophagus or intestine in order to perform the anastomosis. The tissue is positioned between the anvil and the stapling assembly and is typically tied off, for example, by a purse string suture. Thereafter, the anvil member is advanced toward the stapling assembly by rotation of a rotatable knob or wing nut assembly at the proximal end of the instrument. When proper approximation is achieved, the staples are expelled from the fastener assembly. A circular knife typically follows the application of the staples to excise unwanted tissue at the anastomosis site. The instrument is then removed from the lumen of the organ.

To a large degree, the recent explosion in laparoscopic surgical procedures may be attributed to the development of mechanical devices particularly adapted for use in a laparoscopic environment. For example, U.S. Pat. Nos. 5,084,057 and 5,100,520 to Green, et al. describe an endoscopic multiple clip applier which enabled the surgical community to fully realize the potential of endoscopic cholycystectomy. The Green '057 and '420 patents describe, inter alia, a gaseous seal means for obstructing the passage of gas from the insufflated body cavity.

Providing a sealing system for a circular anastomosis instrument is recognized in the art. The present invention provides a uniquely structured sealing system which not only effectively seals the instrument but is easy to manufacture and assemble and does not significantly increase the cost of the instrument.

SUMMARY OF THE INVENTION

The present invention provides a circular anastomosis instrument having means for preventing the flow of gas through the instrument during surgical procedures. Two seals are positioned within the body of the instrument to prevent/inhibit flow of gases through the instrument. The first seal is positioned about a portion of the anvil approximation mechanism of the instrument and is fabricated from polyethylene foam. The second seal is an O-ring positioned proximal of the second seal and between an inner staple firing/compression member and the outer tube of the instrument. The two seals, in combination permit surgeons to perform a circular anastomosis while the patient's body is at least partially insufflated.

BRIEF DESCRIPTION OF THE DRAWINGS

The foregoing features of the present invention will become more readily apparent and may be understood by referring to the following detailed description of an illustrative embodiment of the surgical stapling apparatus and its sealing system, taking in conjunction with the accompanying drawings, in which.

DETAILED DESCRIPTION OF THE INVENTION

Figure 1:
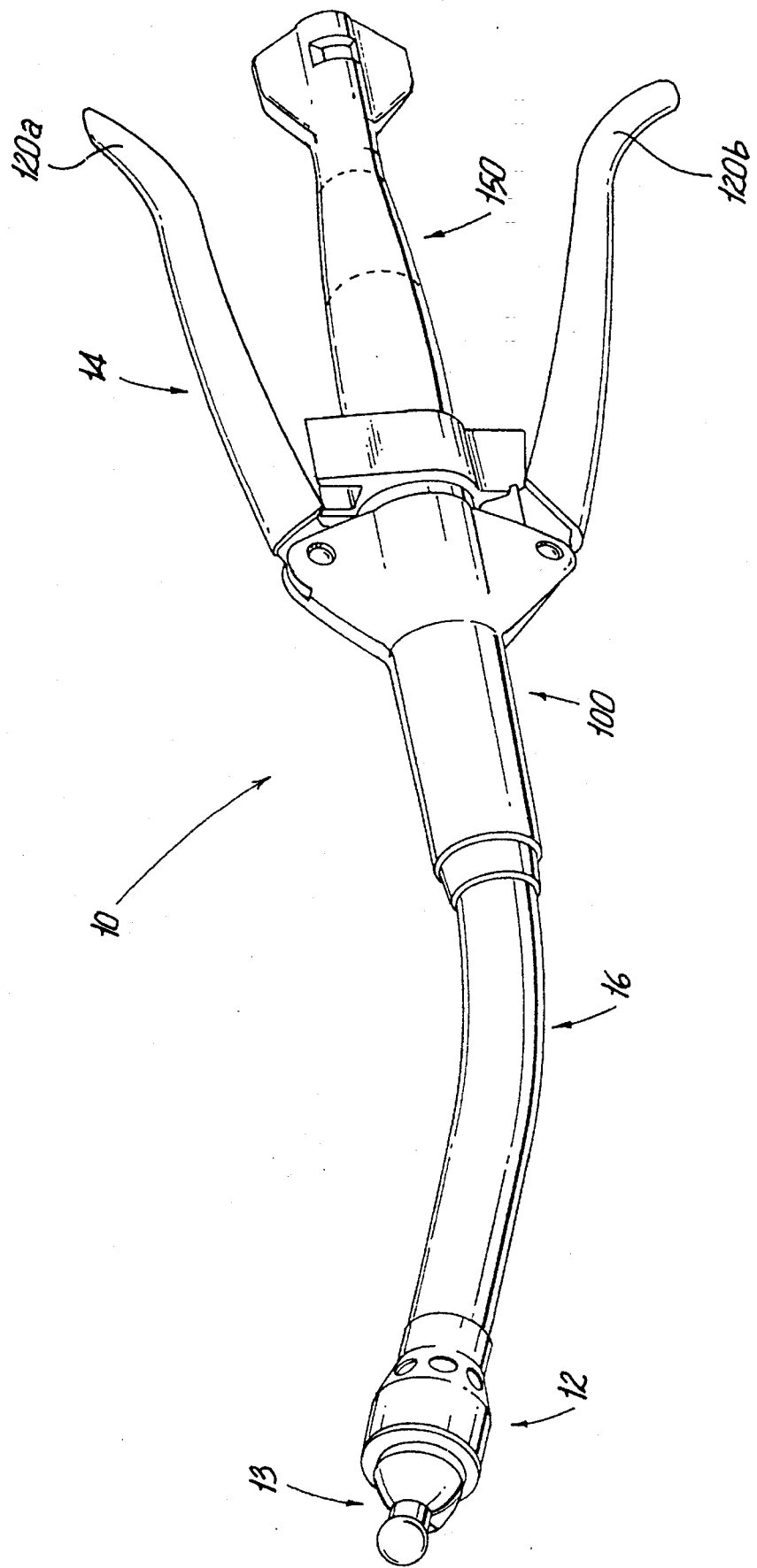
FIG. 1 is a perspective view of a surgical stapler incorporating a sealing system of the present invention.

An illustrative embodiment of a circular anastomosis surgical stapler 10 shown generally in FIG. 1. A typical application of stapler 10 is connecting together two sections of hollow tubular body organ, (e.g., two intestinal sections) by means of an annular array of staples which surrounds a lumen or passageway between the interiors of the connected organ sections. Stapler 10 includes distal stapling assembly 12, anvil member 13, proximal actuator assembly 14 and longitudinal shaft assembly 16 for connecting distal and proximal assemblies and for transmitting actuation forces and motions from the actuator assembly to the stapling assembly. Shaft assembly 16 can be straight or have a longitudinally curved portion as shown. In the particular embodiment shown in the drawing, this curved portion is an arc of a circle and therefore has a generally uniform radius along its length. Detailed descriptions and methods of using similar circular anastomosis devices are disclosed, for example, in commonly assigned U.S. Pat. Nos. 4,576,167, 5,005,749 and 5,119,983, which are incorporated herein by reference. Surgical stapler 10 can also be adapted to apply anastomosis rings and the like.

Figure 2:
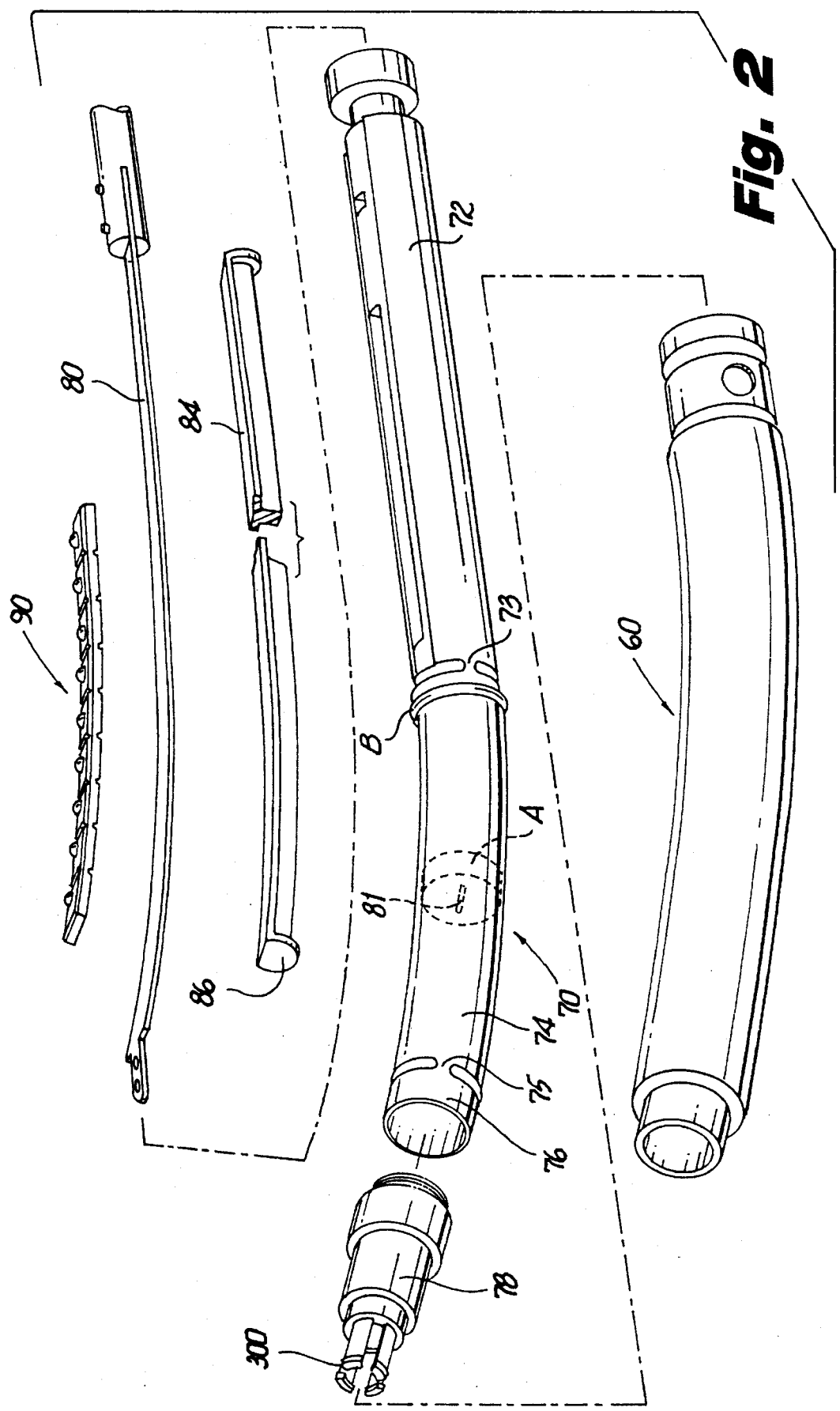
FIG. 2 illustrates an exploded perspective view of a portion of the apparatus of FIG. 1, showing the sealing system of the present invention.

With reference to FIGS. 1 and 2, the proximal end of outer shaft tube 60 is secured to housing 100. Inner tube 70 is disposed within outer shaft tube 60 and is mounted for longitudinal motion relative to tube 60. The distal end of inner tube 70 is threadably connected to extension tube 78 which is also longitudinally movable within outer tube 60. Tubes 70 and 78 constitute a compression member for transmitting a longitudinal compression force produced by operation of handles 120a and 120b of actuator assembly 14 and serve to transmit forces to stapling assembly 12. By squeezing handles 120a and 120b towards each other, tubes 70 and 78 are caused to move distally, thereby causing the ejection of staples, as is known in the art and described in detail in the above commonly assigned patents.

Tube 70 has a straight proximal portion 72, a curved intermediate portion 74, and distal portion 76. Notched sections 73 and 75 separate sections 72 and 74, and 74 and 76 respectively. Sections 73 and 75 are sufficiently narrow to allow some bending or provide some flexibility in tube 70. The material in section 73 may yield when tube 70 is bent or flexed. The distal portion 76 of tube 70 is threadably connected to extension tube 78. The distal end of extension tube 78 includes quills 300 which extend into staple assembly 12 where the quills serve to contact staple pushers (not shown).

Turning to the sealing system of the present invention, two seals A and B are provided. Seal A (shown in phantom) is disposed within tube 70 and has longitudinal aperture 81 to allow band 80 to pass therethrough. Band 80 serves to transmit movement and tension forces from rotatable portion 150 of stapler 10 to anvil member 13, as is known in the art. Preferably, several bands 80 may be used in a stacked relationship, each passing through seal A at aperture 81. Seal A serves to prevent gases from passing through curved portion 74 of inner tube 70. Seal A is preferably at least partially manufactured from a foam-type material, most preferably a polyethylene closed cell foam. The seal can further be provided with sufficient quantities of silicone grease to further facilitate sealing effectiveness.

The second seal B is an O-ring located distal of section 73 at an intermediate portion of inner tube 70. O-ring B can be manufactured from any material suitable for providing a gas seal such as butyl rubber. Tube portion 74 can have a circumferential groove to facilitate placement and securement of seal B thereto.

In operation, when the instrument of the present invention is inserted into an insufflated peritoneum, (e.g., through a natural orifice in the body or through a surgically placed port, such as a cannula), seal A will prevent/inhibit gases from flowing through the interior of tube 70. Seal B will prevent gases flowing between tube 70 and outer tube 60.

It will be understood that the foregoing is only illustrative of the principles of the inventions and that various modifications can be made by those skilled in the art without departing from the scope and spirit of the invention.

What is claimed is:

1. A surgical instrument for performing a circular anastomosis comprising:

a shaft assembly having generally tubular inner compression member and an outer tube with proximal and distal end portions;

a fastener assembly disposed at said outer tube distal end portion;

a housing portion disposed at said outer tube proximal end portion;

an anvil assembly disposed distal of said fastener assembly and means for manipulating said anvil assembly disposed proximal of housing portion, wherein at least one elongate member is disposed within said shaft assembly, said elongate member transferring movement from said anvil manipulating means to said anvil;

an actuator assembly associated with said housing portion for manipulating said inner compression member; and sealing means positioned within said shaft assembly for inhibiting the flow of gases therethrough, said sealing means comprising a first seal fabricated from a generally solid disc of polyethylene foam, said first seal having a longitudinal aperture through which said at least one elongate member passes and having a generally cyclindrical outer surface in contact with an inner surface of said tubular compression member, and a second, O-ring seal disposed intermediate of said compression member and proximal of said first seal, said second seal configured and dimensioned to at least partially contact an outer portion of said tubular compression member and an inner portion of said outer tube.

2. The surgical instrument of claim 1, wherein said first seal is at least partially fabricated from closed cell polyethylene foam.

3. The surgical instrument of claim 1, wherein said second seal is at least partially fabricated from butyl rubber.

4. The surgical instrument of claim 1, wherein said tubular compression member has a circumferential grove on an outer surface thereof and said second seal is at least partially disposed within said groove.

5. The surgical instrument of claim 1, wherein said first seal inhibits the flow of gas between said elongate member and said compression member and said second seal inhibits the flow of gas between said tubular compression member and said outer tube.

* * * * *